US006559328B2

(12) United States Patent
Baum et al.

(10) Patent No.: US 6,559,328 B2
(45) Date of Patent: May 6, 2003

(54) INDIUM SOURCE REAGENT COMPOSITIONS, AND USE THEREOF FOR DEPOSITION OF INDIUM-CONTAINING FILMS ON SUBSTRATES AND ION IMPLANTATION OF INDIUM-DOPED SHALLOW JUNCTION MICROELECTRONIC STRUCTURES

(75) Inventors: Thomas H. Baum, New Fairfield, CT (US); Chongying Xu, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/825,037

(22) Filed: Apr. 3, 2001

(65) Prior Publication Data

US 2001/0021785 A1 Sep. 13, 2001

Related U.S. Application Data

(62) Division of application No. 09/609,516, filed on Jul. 3, 2000, which is a division of application No. 09/218,992, filed on Dec. 22, 1998, now Pat. No. 6,204,402.

(51) Int. Cl.[7] .............................. C07F 5/00; C23C 16/00
(52) U.S. Cl. ............................. 556/40; 556/1; 556/41; 427/248.1; 427/587
(58) Field of Search ............................. 556/1, 40, 41; 427/248.1, 587

(56) References Cited

U.S. PATENT DOCUMENTS 5,840,897 A 11/1998 Kirlin et al. .................... 546/2
6,126,996 A 10/2000 Kirlin et al. ................. 427/252

OTHER PUBLICATIONS

Clark et al., J. Organomet. Chem., vol. 8, No. 3, pp. 427–434 (1967).*
Chung, et al., Can. J. Chem., vol. 52, pp. 3944–3949.
Nomura, et al., Polyhedron, vol. 6, No. 3, pp. 507–512.

* cited by examiner

*Primary Examiner*—Porfirio Nazario-Gonzalez
(74) *Attorney, Agent, or Firm*—Margaret Chappuis; Steven J. Hultquist

(57) ABSTRACT

An indium precursor composition having utility for incorporation of indium in a microelectronic device structure, e.g., as an indium-containing film on a device substrate by bubbler or liquid delivery MOCVD techniques, or as a dopant species incorporated in a device substrate by ion implantation techniques. The precursor composition includes a precursor of the formula $R_1R_2InL$ wherein: $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl, or $C_1$–$C_6$ perfluoroalkyl; and L is β-diketonato or carboxylate. Indium-containing metal films may be formed on a substrate, such as indium-copper metallization, and shallow junction indium ion-implanted structures may be formed in integrated circuitry, using the precursors of the invention.

13 Claims, 3 Drawing Sheets

INDIUM SOURCE REAGENT COMPOSITIONS, AND USE THEREOF FOR DEPOSITION OF INDIUM-CONTAINING FILMS ON SUBSTRATES AND ION IMPLANTATION OF INDIUM-DOPED SHALLOW JUNCTION MICROELECTRONIC STRUCTURES

This is a division of U.S. application Ser. No. 09/609,516, filed Jul. 3, 2000, which is a division of U.S. application Ser. No. 09/218,992, filed on Dec. 22, 1998 now U.S. Pat. No. 6,204,402.

GOVERNMENT RIGHTS IN INVENTION

The invention hereof was made with Government funding assistance under Contract No. DMI - 9660730 awarded by the National Science Foundation. The Government has certain rights in the invention.

BACKGROUND OF THE INVENTION

1. Field of the Invention

This invention relates to an indium source reagent composition having utility for incorporation of indium in a microelectronic device structure, e.g., as an indium-containing film on a device substrate by bubbler or liquid delivery MOCVD techniques, or as a dopant species incorporated in a device substrate by ion implantation techniques. The invention also relates to such semiconductor fabrication techniques for using the indium source reagent of the invention, as well as to microelectronic device structures incorporating indium by use of such source reagent and techniques.

2. Description of the Related Art

In the field of semiconductor manufacturing, indium is a material of considerable current and future technological importance.

With the emergence and proliferation of copper as a preferred material in metallization for formation of conductor transmission lines of integrated circuitry devices, copper-indium (Cu/In) alloys are of great interest for improving the long-term performance, electro-migration resistance and reliability of copper-based interconnects. Indium-containing III–V semiconductor materials also will play an increasingly important role in the development of electronic and opto-electronic devices.

The most commonly used In precursors for the deposition of In-based materials are trialkylindium, such as trimethylindium and triethylindium. For the chemical vapor deposition (CVD) of Cu/In alloys, such conventional In precursors are not compatible with currently used Cu precursors, when multiple source precursors (for In and Cu) are introduced. In addition, the conventional In precursors are extremely sensitive to air, oxygen and moisture, leading to vigorous exothermic reactions, fire and explosions when exposed to such ambient atmospheric constituents.

Indium also is of great current interest in the microelectronics field as a potential dopant species for the formation of doped shallow junctions in integrated circuitry devices, since shallow device junctions enable high performance devices to be fabricated at lower switching voltages than are required for junctions of greater depth. Further, in relation to other dopant species that may be employed for forming doped junction structures by conventional ion implantation techniques, indium has the significant advantage that its size and mass allow lower implant energies to be used, provided that useful beam currents of In ions can be obtained.

The beam current is a critical aspect of the ion implantation operation as practiced in conventional ion implanter systems, and is strongly precursor material-dependent in character. Specifically, the vaporization and delivery of the precursor for ionization and ion beam transport of the implant species typically requires a material of suitable volatility and transport characteristics, but volatile liquids and solids when used as precursors also create a potential risk of introduction of reactive species that are susceptible to side-reactions and also create the potential for contamination of the substrate and disruption of the desired device characteristics.

Given these circumstances, there is a compelling need in the art for new In precursors suitable for deposition of In-based materials or ion implantation of In in semiconductor device structures.

SUMMARY OF THE INVENTION

This invention relates in one aspect to an indium source reagent composition useful for incorporating indium in a microelectronic device structure, e.g., as an indium-containing film on a device substrate by bubbler or liquid delivery MOCVD techniques, or as a dopant species incorporated in a device substrate by ion implantation techniques.

The invention also relates to such semiconductor fabrication techniques for using the indium source reagent of the invention, as well as to microelectronic device structures incorporating indium by use of such source reagent and techniques.

In one aspect, the invention relates to an indium precursor composition of the formula:

$$R_1R_2InL$$

wherein:

$R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, or $C_1$–$C_6$ fluoroalkyl $C_1$–$C_6$ perfluoroalkyl; and L is β-diketonato or carboxylate.

Another aspect of the invention relates to an indium precursor composition of the formula:

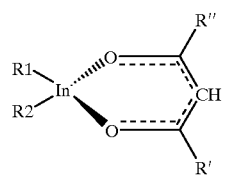

wherein:

R' and R" may be the same or different and are independently selected from H, $C_6$–$C_{10}$ aryl, $C_6$–$C_{10}$ perfluoroaryl, $C_1$–$C_6$ alkyl, $C_1$–$C_6$ fluoroalkyl, and $C_1$–$C_6$ perfluoroalkyl; and $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl, or $C_1$–$C_6$ perfluoroalkyl.

Still another aspect of the invention relates to a method of making a dialkyl(β-diketonate)indium(III) compound, by the reaction:

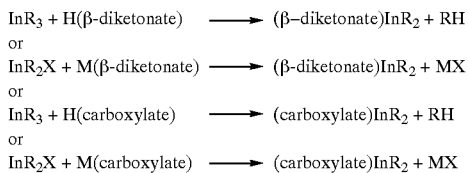

wherein:
  each R may be same or different and is independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl and;
  M is selected from Li, Na, or K and;
  X is selected from F, Cl, Br or I.

In a further aspect, the invention relates to a liquid delivery metal-organic chemical vapor deposition process for forming a In-containing film on a substrate, comprising:
  providing a liquid precursor composition including an indium precursor of the formula:

$R_1R_2InL$ wherein:
  $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl; and
  L is β-diketonato or carboxylate;
  flash vaporizing the precursor to form a precursor vapor;
  transporting the precursor vapor to a chemical vapor deposition reactor containing a substrate element;
  contacting the precursor vapor with the substrate element in the chemical vapor deposition reactor under chemical vapor deposition conditions, to form an In-containing film on the substrate element.

A further aspect of the invention relates to a method of ion implantation of In+ ions in a substrate, comprising ionizing an indium precursor composition to produce an ionization product including In+ ions, separating In+ ions from the ionization product, and directing the separated In+ ions under ion implantation conditions into the substrate, wherein the indium precursor composition comprises an indium precursor of the formula:

$R_1R_2InL$ wherein:
  $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl; and
  L is β-diketonato or carboxylate.

Still another aspect of the invention relates to a microelectronic device structure comprising a shallow junction region containing IN+ ions derived from ionization of an indium precursor composition comprising an indium precursor of the formula:

$R_1R_2InL$ wherein:
  $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl; and
  L is β-diketonato or carboxylate.

The invention further relates to a microelectronic device structure including conductor transmission lines comprising an indium-copper composition formed by chemical vapor deposition of indium and copper from precursor material therefor, wherein said precursor material comprises an indium precursor of the formula:

$R_1R_2InL$ wherein:
  $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl; and
  L is β-diketonato or carboxylate.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
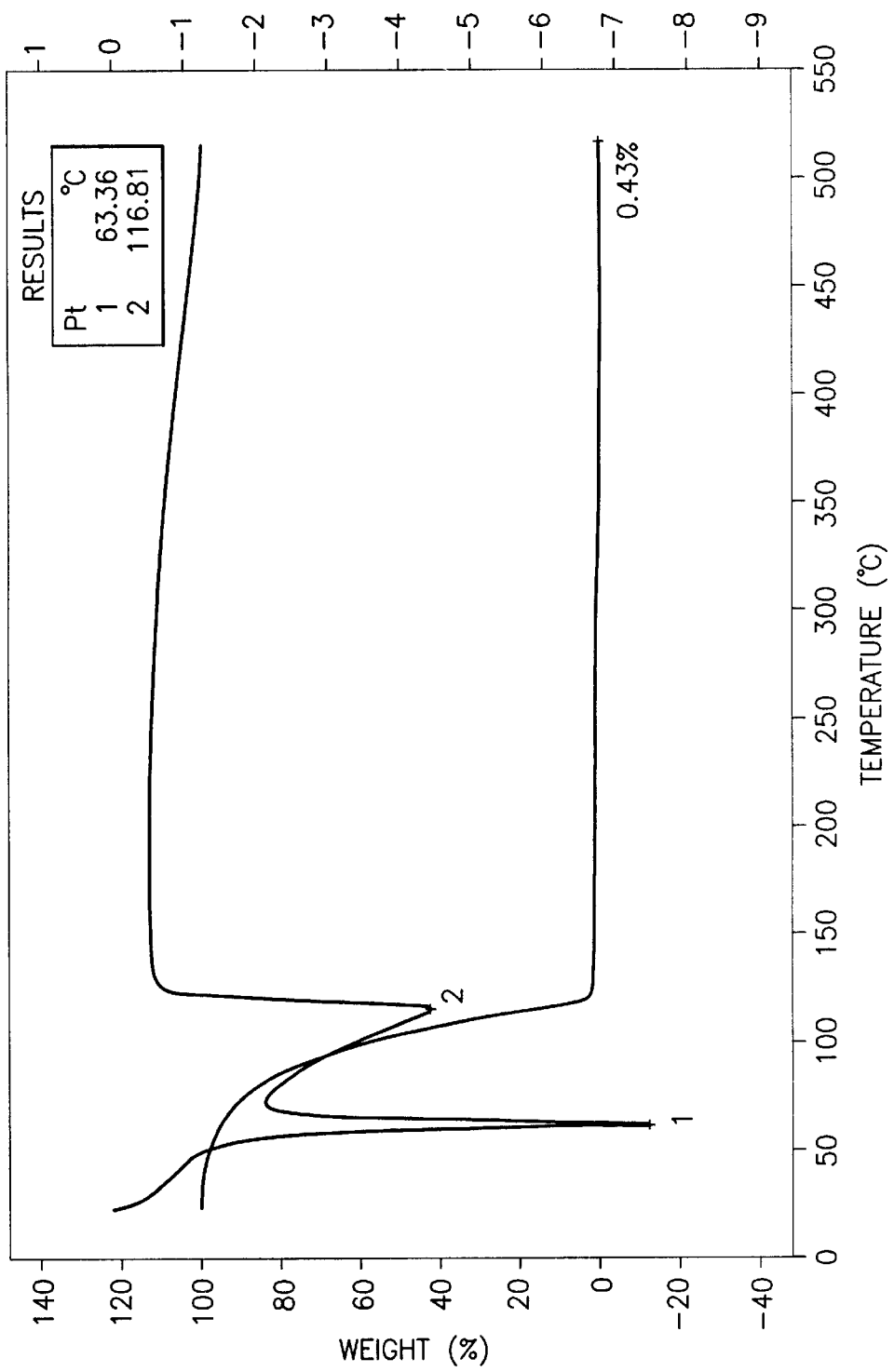
FIG. 1 is an STA plot for (hfac)In(CH$_3$)$_2$.

The present invention is based on the discovery that when one or more of the alkyl groups of a trialkylindium compound is replaced by a β-diketonate or carboxylate, its reactivity decreases significantly, while the volatility of the resulting compound is substantially increased, to a level that has been found to be consistent with utility of the compound for chemical vapor deposition and ion implantation. Further, such substituted organoindium compounds have been found to be unexpectedly stable in exposure to air, oxygen and moisture.

The disclosures of the following United States patents and patent applications are hereby incorporated herein by reference in their entirety:

U.S. patent application Ser. No. 08/835,768 filed Apr. 8, 1997 in the names of Thomas H. Baum, et al.;

U.S. patent application Ser. No. 08/484,654 filed Jun. 7, 1995 in the names of Robin A. Gardiner et al.;

U.S. patent application Ser. No. 08/414,504 filed Mar. 31, 1995 in the names of Robin A. Gardiner et al.;

U.S. patent application Ser. No. 08/280,143 filed Jul. 25, 1994, in the names of Peter S. Kirlin, et al.;

U.S. patent application Ser. No. 07/927,134, filed Aug. 7, 1992 in the same names;

U.S. patent application Ser. No. 07/807,807, filed Dec. 13, 1991 in the names of Peter S. Kirlin, et al., now issued as U.S. Pat. No. 5,204,314;

U.S. patent application Ser. No. 08/181,800 filed Jan. 15, 1994 in the names of Peter S. Kirlin, et al., and issued as U.S. Pat. No. 5,453,494;

U.S. patent application Ser. No. 07/918,141 filed Jul. 22, 1992 in the names of Peter S. Kirlin, et al., and issued Jan. 18, 1994 as U.S. Pat. No. 5,280,012;

U.S. patent application Ser. No. 07/615,303 filed Nov. 19, 1990;

U.S. patent application Ser. No. 07/581,631 filed Sep. 12, 1990 in the names of Peter S. Kirlin, et al., and issued Jul. 6, 1993 as U.S. Pat. No. 5,225,561; and U.S. patent application Ser. No. 07/549,389 filed Jul. 6, 1990 in the names of Peter S. Kirlin, et al.

The compounds of the present invention have the formula:

$$R_1R_2InL$$

wherein:

$R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl; and L is β-diketonato or carboxylate.

Preferred β-diketonate In precursors of the invention have the formula:

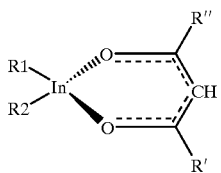

wherein:

R' and R" may be the same or different and are independently selected from H, $C_6$–$C_{10}$ aryl, $C_6$–$C_{10}$ perfluoroaryl, $C_1$–$C_6$ alkyl, $C_1$–$C_6$ fluoroalkyl, and $C_1$–$C_6$ perfluoroalkyl; and $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl.

The β-diketonate moiety of the In precursor compound of the invention may be any suitable β-diketonate moiety that can be coordinated to the In metal atom and is effective to form a complex of the desired stability, solubility and volatility characteristics. Illustrative of β-diketonate species that may be usefully employed in the broad practice of the present invention are the following:

2,2,6,6-tetramethyl-3,5-heptanedionate ("thd");

2,2,6-trimethyl-3,5-heptanedione ("Hthd");

1,1,1,2,2,3,3,-heptafluoro-7,7-dimethyl-octane-4,6-dionate ("fod");

acetylacetonate ("acac");

1,1,1-trifluoroacetylacetonate ("tfac");

1,1,1,5,5,5,-hexafluoroacetylacetonate ("hfac"); and 2,2,7-trimethyl-3,5-octanedionate ("tod").

The precursor may for example be of the formula $R_1R_2In$ (hfac), wherein $R_1$ and $R_2$ may be same or different and are independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl. Specific examples of the precursor include $(CH_3)_2In(hfac)$ and $(CF_3)_2In(hfac)$.

The precursor compounds of the invention can be synthesized by the reaction:

$$InR_3 + H(\beta\text{-diketonate}) \longrightarrow (\beta\text{-diketonate})InR_2 + RH$$

or $$InR_2X + M(\beta\text{-diketonate}) \longrightarrow (\beta\text{-diketonate})InR_2 + MX$$

or $$InR_3 + H(\text{carboxylate}) \longrightarrow (\text{carboxylate})InR_2 + RH$$

or $$InR_2X + M(\text{carboxylate}) \longrightarrow (\text{carboxylate})InR_2 + MX$$

wherein:

each R may be same or different and is independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl or $C_1$–$C_6$ perfluoroalkyl and;

M is selected from Li, Na, or K and;

X is selected from F, Cl, Br or I.

Dialkyl(β-diketonate)indium(III) compounds of the invention can be synthesized by a direct reaction of trialkylindium and β-diketone as expressed in the equation 1:

$$InR_3 + H(\beta\text{-diketonate}) \longrightarrow (\beta\text{-diketonate})InR_2 + RH \quad (1)$$

wherein:

each R may be the same or different and is alkyl.

A corresponding reaction can be carried out to form the dialkyl(carboxylate)indium (III) compounds of the invention, using a carboxylic acid as a coreactant with the trialkylindium starting material, wherein the carboxylate may be formate, trifluoroacetate, pivalate and alkyl, fluoroalkyl or perfluoroalkyl carboxylate.

Dialkyl(β-diketonate)indium(III) compounds of the invention can be also synthesized by a salt-elimination reaction as expressed in equation 2:

$$InR_2X + M(\beta\text{-diketonate}) \longrightarrow (\beta\text{-diketonate})InR_2 + MX \quad (2)$$

wherein each R may be the same or different and is alkyl. A corresponding reaction can be carried out to form the dialkyl(carboxylate)indium (III) compounds of the invention, using a carboxylic acid as a coreactant with the trialkylindium starting material, wherein the carboxylate may be formate, trifluoroacetate, pivalate and alkyl, fluoroalkyl or perfluoroalkyl carboxylate.

The (β-diketonate)$InR_2$ and (carboxylate)$InR_2$ compositions of the invention are highly effective source reagents for use in the deposition of In-containing materials, and may readily be used in place of conventional In precursors. The compositions and methodology of the invention provide the following advantages:

1). the precursor compositions of the invention are: i) air and moisture stable, ii) highly volatile and thermally stable, iii) compatible with Cu CVD precursors; and 2). MOCVD and ion implant processes using the precursor compositions of the invention provide a safer, more reliable and more effective way for depositing In-containing materials or of implanting In in substrate materials.

The In-containing materials, which can be metallic alloy or III–V semiconductor materials, can be deposited by thermal decomposition of (dialkyl)In(III)(β-diketonate) precursors. For the deposition of Cu/In alloy, the alloy films may be formed by depositing In metal onto Cu films directly, or by depositing the two elements simultaneously from dual bubblers.

In some cases, it may be advantageous to decompose the precursor in the presence of a reducing co-reactant (e.g., $H_2$) to preferentially deposit In metal.

The alloy films may also be deposited using a single bubbler for delivering a mixture of the In and Cu precursors.

For the deposition of III–V semiconductor materials, the precursor can be decomposed in the presence of Group V co-reagents (e.g., $AsH_3$, $PH_3$, or $SbH_3$) to deposit InAs, InP or InSb, respectively.

In the broad practice of the present invention involving the use of the precursors for deposition of In-containing films, either a bubbler delivery system or a liquid delivery technique can be used for deposition of the In-containing materials. In the liquid delivery approach, the liquid precursor can be delivered for the CVD of the In-containing material thin films using ($\beta$-diketonate)In(III)(dialkyl) in a suitable solvent medium that is compatible with the In precursor, e.g., hydrocarbons (aliphatic or aromatic), organic amines, polyamines, organic ethers, organic esters, alkyl nitrites, alkanols, glymes, tetraglymes, and solvent mixtures of suitable solvent species such as for example alkane solvent species in combination with amine or polyamine solvent species. In the bubbler delivery approach the precursor can be delivered for the CVD of the In-containing material thin films using ($\beta$-diketonate)In(III)(dialkyl) neat.

Specific types of solvents may include: glyme solvents having from 1 to 20 ethoxy repeating units, $C_2$–$C_{12}$ alkanols, organic ethers selected from the group consisting of dialkyl ethers comprising $C_1$–$C_6$ alkyl moieties, $C_4$–$C_8$ cyclic ethers, $C_8$–$C_{40}$ crown, $O_1$–$O_{20}$ ethers wherein the prefixed $C_i$ range is the number i of carbon atoms in the ether compound and the suffixed $O_i$ range is the number i of oxygen atoms in the ether compound, $C_6$–$C_{12}$ aliphatic hydrocarbons, $C_6$–$C_{18}$ aromatic hydrocarbons, and organic esters, amines and polyamines. Specific solvent species include tetrahydrofuran, alkyl acetate, tetraglyme and $C_3$–$C_8$ alkanols.

It will be recognized that the foregoing is of an illustrative character, and that a wide variety of solvent media may be employed in the broad practice of the invention.

The liquid delivery process of the invention may include the provision of multiple precursors including the In precursor of the invention and other precursors, such as a Cu precursor for the formation of indium-copper interconnects, an aluminum precursor for AlInN film formation, a Ga precursor for GaInN film formation, etc. The respective precursor compositions may be combined in a single multicomponent precursor medium as a "cocktail" including all of the metal species to be deposited to form the product multicomponent metal film, or alternatively, separate precursor compositions may be separately vaporized and the resulting vapor then combined in the manner more fully described in co-pending U.S. patent application Ser. No. 08/758,599 filed Nov. 27, 1996 in the names of J. Roeder et al. for "Multiple Vaporizer Reagent Supply System for Chemical Vapor Deposition Utilizing Dissimilar Precursor Compositions", the disclosure of which hereby is incorporated herein by reference in its entirety.

The invention thus contemplates the provision of single as well as multiple vaporizer zones for generating the precursor vapor from the corresponding precursor composition(s) including the In precursor of the invention. The flash vaporization may be carried out in a single vaporizer to generate the In precursor vapor, or alternatively, multiple vaporizer units may be employed, for flash vaporization of respective precursor compositions including the separate In precursor composition of the invention. Where the precursor compositions include solvent media, different solvent media may be employed in the respective ones of the multiple precursor compositions.

The flash vaporizer zone may be constructed and arranged as more fully described in U.S. Pat. No. 5,536,323 issued Jul. 16, 1996 in the names of Peter S. Kirlin et al., U.S. Pat. No. 5,711,816 issued Jan. 27, 1998 in the names of Peter S. Kirlin et al., and U.S. Pat. No. 5,204,314 issued Apr. 20, 1993 in the names of Peter S. Kirlin et al., the disclosures of which hereby are incorporated herein by reference in their entireties.

A chemical vapor deposition reactor may also be provided in precursor vapor-receiving relationship to the vaporizer or the bubbler, and constructed and arranged as more fully described in the incorporated by reference U.S. Patents described in the preceding paragraph.

The precursor vapor deriving from flash vaporization of the precursor composition is flowed directly or carried by a carrier gas into the chemical vapor deposition reactor. The carrier gas may be of any suitable type that is non-deleteriously employed with the precursor vapor. Illustrative of suitable gas species which may potentially be useful in the broad practice of the present invention are argon, nitrogen, helium, ammonia, etc. The carrier gas functions to entrain and mix with the precursor vapor to provide a precursor gas mixture which is transmitted to the chemical vapor deposition chamber.

The precursor vapor mixture may be mixed in the chemical vapor deposition reactor with an oxidizing co-reactant gas if an In-containing metal oxide film is desired to be formed. The oxidizing co-reactant gas may be of any suitable type providing an oxygen-containing environment in which the In-containing metal oxide film may be formed on the substrate.

The substrate for such purpose may be suitably retained at a desired temperature, as for example in the range of from about 100° C. to about 1200° C., by appropriate heating means, which may for example utilize a resistably heated susceptor structure on which the substrate is mounted, infrared heating means, inductively coupled heating arrangements, or other heat transfer or heat exchange means whereby the substrate is maintained at the desired temperature for deposition on the substrate of the desired In-containing material films.

The oxidizing co-reactant gas when employed may comprise oxygen gas ($O_2$), ozone, singlet oxygen, $N_2O$, or other oxic gas, or active oxidizing species, e.g., from a remote plasma source. The chemical vapor deposition reactor is maintained at a suitable pressure, e.g., of from about 0.1 torr to about 760 torr, and the chemical vapor deposition is carried out for sufficient time to provide growth of the In-containing material films to a desired thickness, as for example a thickness in the range of from about 0.01 micron to about 200 microns. The chemical vapor deposition reactor may be equipped with a showerhead-type distributor for influent gaseous/vapor streams, e.g., a showerhead device of the type described in U.S. patent application Ser. No. 08/402,142 filed Mar. 10, 1995 in the names of Peter C. Van Buskirk et al. for "Showerhead-Type Discharge Assembly for Delivery of Source Reagent Vapor to a Substrate, and CVD Process Utilizing Same " and U.S. patent application Ser. No. 08/621,088 filed Mar. 22, 1996 in the names of Peter C. Van Buskirk et al. for "Interiorally Partitioned Vapor Injector for Delivery of Source Reagent Vapor Mixtures for Chemical Vapor Deposition," the disclosures of which hereby are incorporated by reference herein in their entireties.

The precursors of the invention may be used to provide In-Cu interconnects in microelectronic device manufacture, as well as the formation of III–V semiconductor materials for electronic and optoelectronic applications.

In ion implantation applications, the precursors of the invention may be used to generate a suitable ion beam of In+ for ion implantation of indium ions in a microelectronic device structure. For such purpose, a bubbler or liquid delivery technique may be used to achieve transport of the precursor to the ion implanter. Compositions of the invention for ion implantation may suitably comprise perfluorinated (β-diketonate)InR$_2$ or (acetate)InR$_2$ compositions which by virtue of their fluorine substituents act to assist the cleaning and etching of the ion source and implanter electrooptic components, thereby serving to remove carbonaceous deposits from such equipment.

The In precursors of the invention enable In+ doping to form shallow junctions for the manufacture of high performance microelectronic devices.

Examples of microelectronic device structures that are usefully fabricated utilizing the In deposition and implantation processes and In precursor compositions of the invention include transistors such as metal-oxide-semiconductor field effect transistors (MOSFETs), NMOS, PMOS and CMOS transistor devices, MESFETs, bipolar junction transistors, capacitor structures, memory cells, etc.

The indium precursor of the invention may also be utilized for forming In—Cu metallization elements, e.g., conductor transmission lines and interconnects, in integrated circuitry applications.

The features and advantages of the invention are more fully shown by the following non-limiting examples, wherein all parts and percentages are by weight, unless otherwise expressly stated.

EXAMPLE 1

In this example, (hfac)In(CH$_3$)$_2$ was synthesized, and utilized for CVD of In.

1). Synthesis of (hfac)In(CH$_3$)$_2$: The general reaction was carried out under a steady flow of nitrogen. A Schlenk flask was charged with 4.80 g (30 mmol) of trimethylindium and 20 mL diethyl ether. 1,1,1,5,5,5-hexafluoroacetylacetone (6.20 g, 30 mmol) was added dropwise to the magnetically stirred solution at about −10° C. After the addition, the clear solution was stirred for one hour at room temperature. Removal of volatiles yielded 9.5 g (~90%) white needle-shaped crystals.

2). Characterization: The crystalline product was characterized by solution NMR ($^1$H and $^{13}$C). The NMR data were consistent with the molecular formula of (hfac)In(CH$_3$)$_2$. Sublimation and STA results (see FIG. 1) showed that (hfac)In(CH$_3$)$_2$ can be sublimated intact. STA data also showed that (hfac)In(CH$_3$)$_2$ has a low melting point (63° C.) and thus may be used as a liquid In source for CVD at a temperature above 63° C.

To determine the degree of oligomerization of (hfac)In(CH$_3$)$_2$ in solid state, single crystals were grown by sublimation of the compound at room temperature under an atmospheric pressure. Suitable crystal material was selected and characterized by single crystal X-ray diffraction. The molecular structure is shown in the Ortep diagram of FIG. 2.

3). Stability study: i). A small amount of crystalline (hfac)In(CH$_3$)$_2$ was exposed to air in a vial for at least 2 days. No reactions were observed visually or by $^1$H NMR. These observations revealed that (hfac)In(CH$_3$)$_2$ is stable to air and water moisture.

Stability study: ii). To study the compatibility of (hfac)In(CH$_3$)$_2$ with (hfac)Cu(I)A, wherein A=a neutral Lewis base ligand, a small amount of (hfac)In(CH$_3$)$_2$ and (hfac)Cu(I)A, where A=dimethylcyclooctadiene ("DMCOD") or 2-methyl-1-hexen-3-yne ("MHY"), were mixed and dissolved in C$_6$D$_6$ in a NMR tube. $^1$H NMR results indicated that no reaction took place.

For comparison, trimethylindium and (hfac)Cu(I)A were mixed together in C$_6$D$_6$; a yellow gel precipitation formed initially, then the yellow precipitation quickly turned into black particles. Further study revealed the reaction led to the formation of Cu metal (black particles) and (hfac)In(CH$_3$)$_2$.

Figure 3:
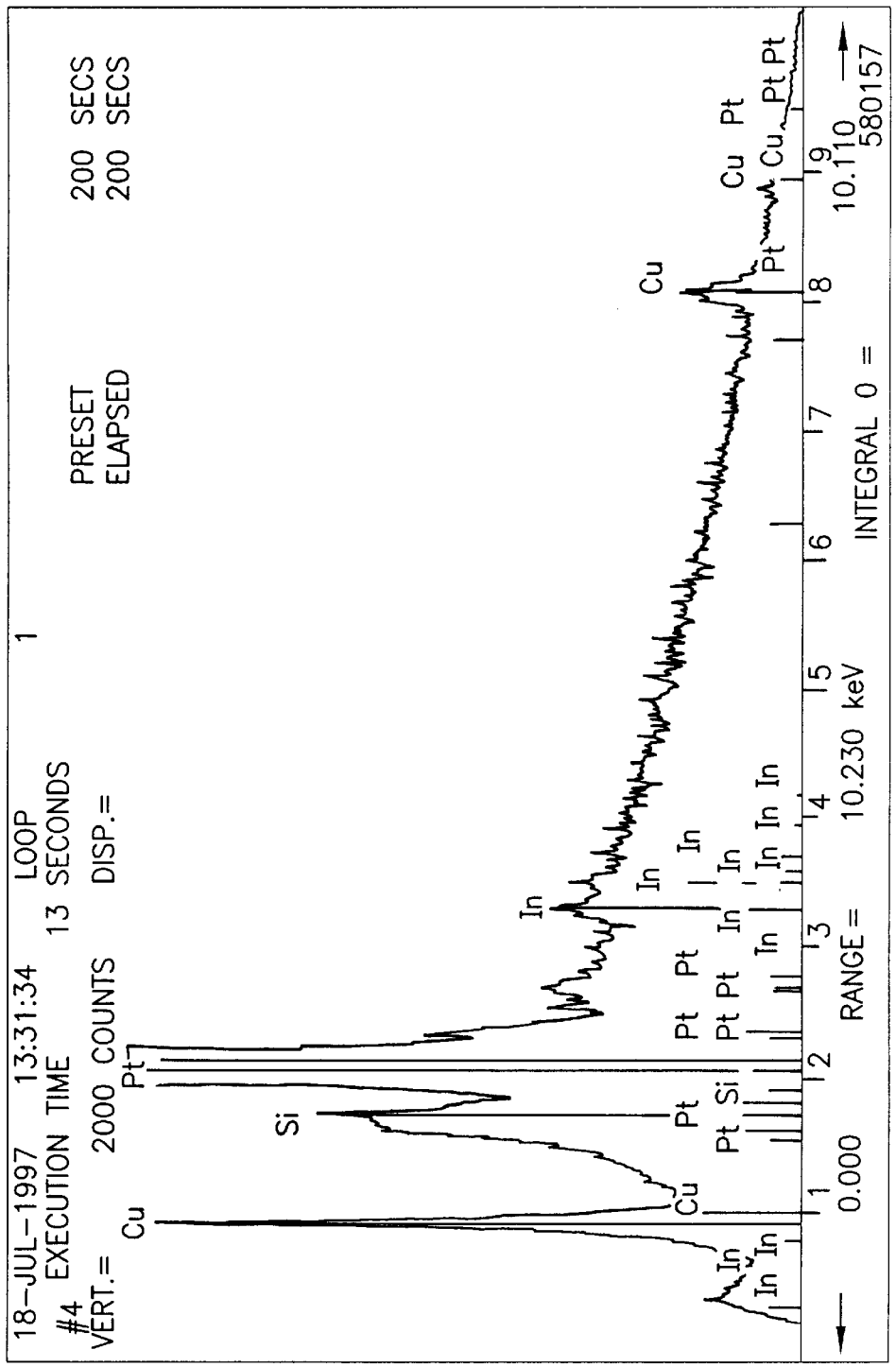
FIG. 3 is an Energy Dispersive Spectroscopy (EDS) spectrum of Cu(In) alloy deposited from (hfac)In(III)(CH$_3$)$_2$.
Figure 2:
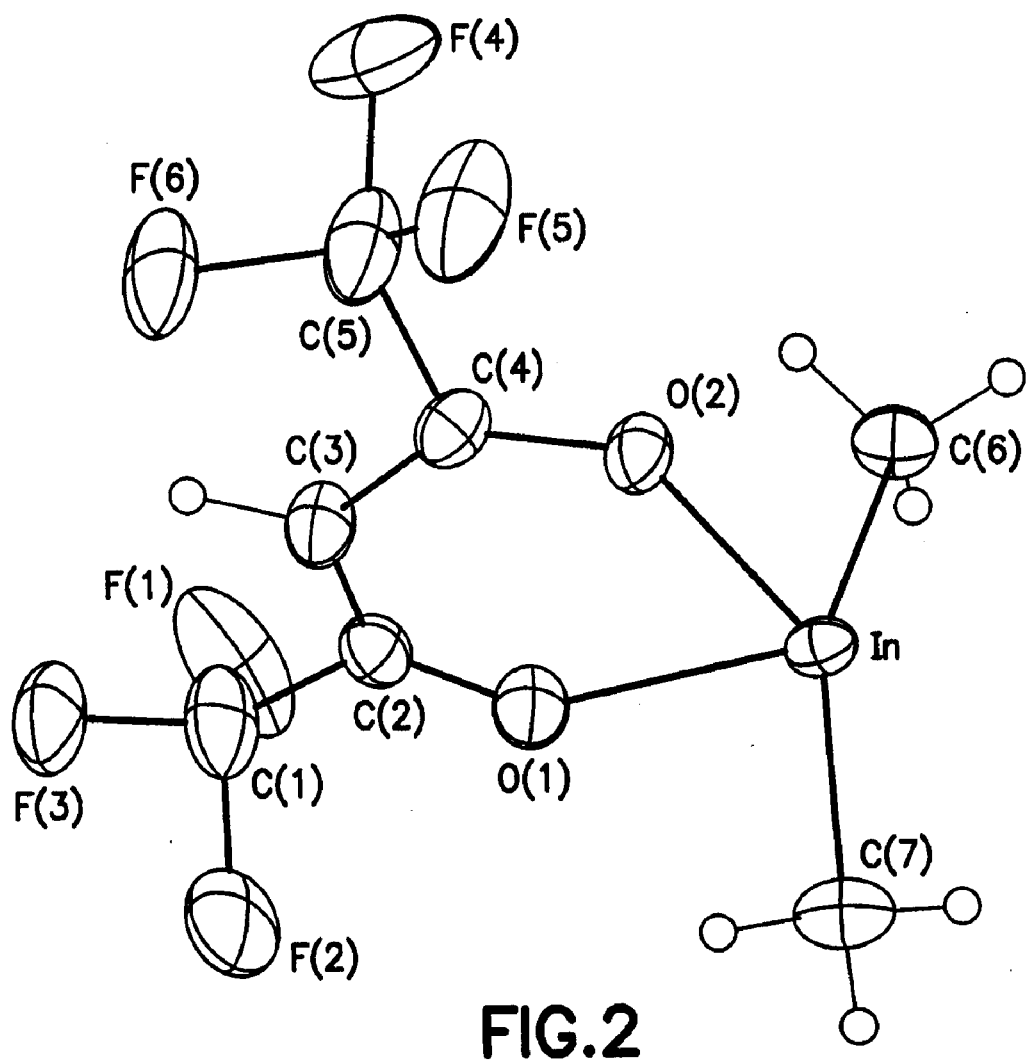

4). CVD study: The chemical vapor deposition of Cu(In) alloys was studied using (hfac)In(II)(CH$_3$)$_2$ as a precursor. Copper-indium alloys were formed by depositing In on Cu-coated Pt/Si substrates at 300° C. in a warm-wall belljar CVD reactor without carrier gas. The reactor pressure was maintained between 0.9–2.0 Torr. Under these conditions, a Cu(In) alloy film was formed. A film was analyzed by Energy Dispersive Spectroscopy (EDS) and the spectrum is shown in FIG. 3. Semi-quantitative EDS results revealed that the ratio of In:Cu:Pt of the film was 1:5:4.

While the invention has been illustratively described herein with reference to various embodiments and disclosed features, it will be appreciated that the invention is not thus limited, but rather extends to and encompasses numerous variations, modifications and other embodiments. Accordingly, the invention is intended to be broadly construed and interpreted as including all such variations, modifications and other embodiments within the spirit and scope thereof, as hereinafter claimed.

What is claimed is:

1. A method of making a (β-diketonate)InR$_2$ compound, by the reaction:

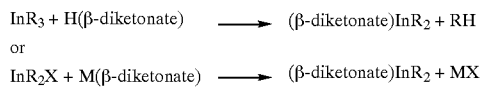

wherein each R may be same or different and is independently selected from C$_6$–C$_{10}$ aryl, C$_6$–C$_{10}$ fluoroaryl, C$_6$–C$_{10}$ perfluoroaryl, C$_1$–C$_6$ alkyl, C$_1$–C$_6$ fluoroalkyl, or C$_1$–C$_6$ perfluoroalkyl, with the proviso that R substituents in InR$_3$ are not all methyl or all butyl;

M is selected from Li, Na and K; and

X is selected from F, Cl, Br, and I.

2. The method of claim 1, wherein the reaction comprises:

3. The method of claim 1, wherein each R may be same or different and is independently selected from C$_1$–C$_6$ alkyl, C$_1$–C$_6$ fluoroalkyl, or C$_1$–C$_6$ perfluoroalkyl.

4. The method of claim 1, wherein each R may be same or different and is independently selected from C$_1$–C$_6$ alkyl.

5. The method of claim 1, wherein each R may be same or different and is independently selected from C$_1$–C$_6$ fluoroalkyl.

6. The method of claim 1, wherein each R may be same or different and is independently selected from C$_1$–C$_6$ perfluoroalkyl.

7. The method of claim 1 wherein R is methyl and β-diketonate is 1,1,1,5,5,5-hexafluoroacetylacetonate.

8. A method of making a (β-diketonate)InR$_2$ compound, by the reaction:

wherein each R may be same of different and is independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl, or $C_1$–$C_6$ perfluoroalkyl;

M is selected from Li, Na and K; and

X is selected from F, Cl, Br, and I.

9. A method of making a (carboxylate)$InR_2$ compound, by the reaction:

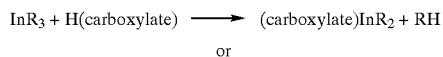

wherein:

each R may be same or different and is independently selected from $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl, and $C_1$–$C_6$ perfluoroalkyl, with the proviso that R substituents in $InR_3$ are not all methyl or all butyl;

M is selected from Li, Na and K; and

X is selected from F, Cl, Br, and I.

10. The method of claim 9, wherein each R may be same or different and is independently selected from $C_1$–$C_6$ alkyl, $C_1$–$C_{16}$ fluoroalkyl, or $C_1$–$C_6$ perfluoroalkyl.

11. The method of claim 9, wherein each R may be same or different and is independently selected from $C_1$–$C_6$ alkyl.

12. The method of claim 9, wherein each R may be same or different and is independently selected from $C_1$–$C_6$ fluoroalkyl.

13. The method of claim 9, wherein each R may be same or different and is independently selected from $C_1$–$C_6$ perfluoroalkyl.

* * * * *

UNITED STATES PATENT AND TRADEMARK OFFICE
CERTIFICATE OF CORRECTION

PATENT NO.    : 6,559,328 B2
DATED         : May 6, 2003
INVENTOR(S)   : Thomas H. Baum et al.

Figure 2:
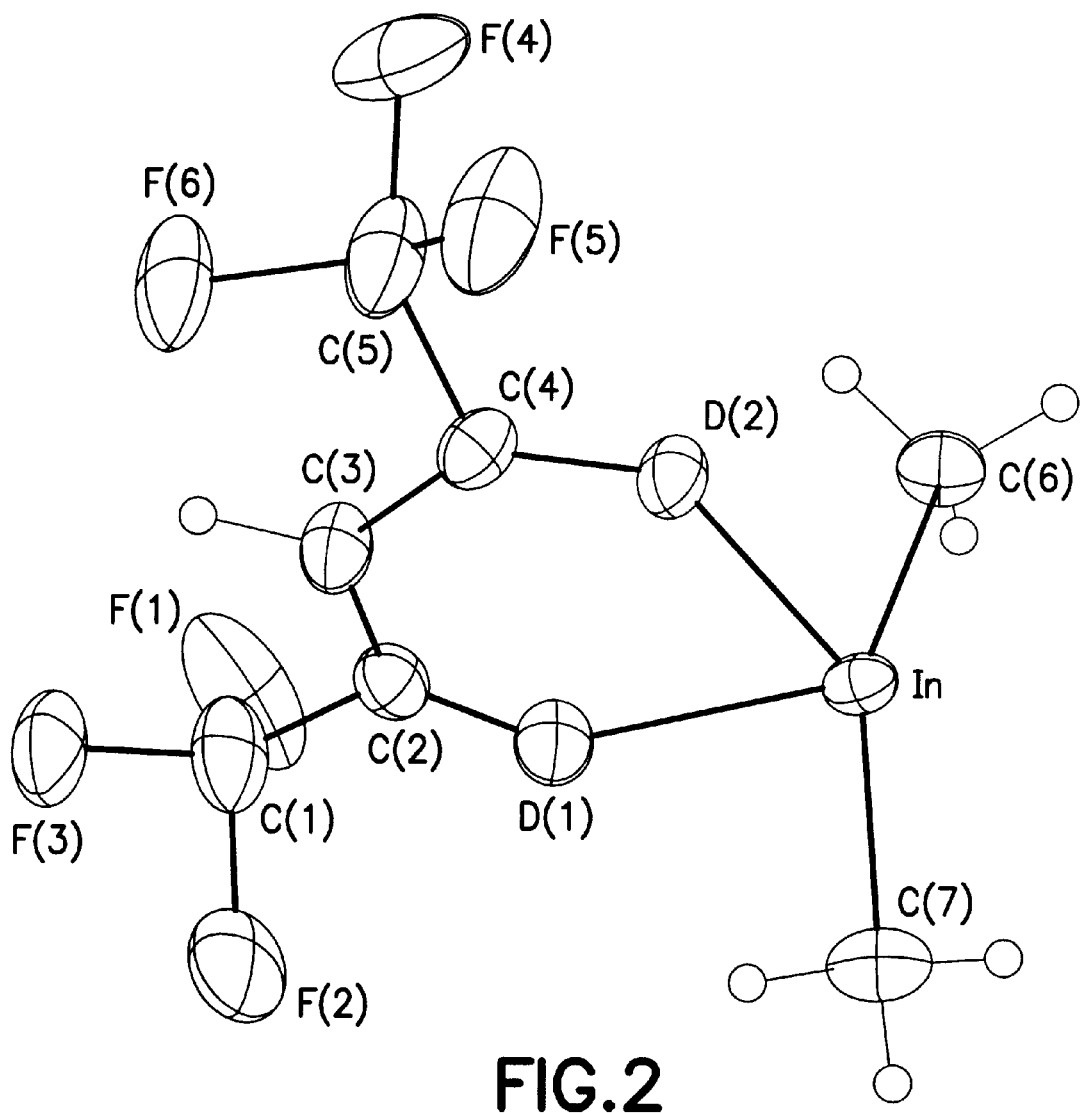
FIG. 2 is an Ortep diagram of the molecular structure of (hfac)In(CH$_3$)$_2$.

It is certified that error appears in the above-identified patent and that said Letters Patent is hereby corrected as shown below:

Drawings,
Sheet 2 of 3, delete FIG. 2 replace FIG 2 as attached on the next page.

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,559,328 B2
DATED         : May 6, 2003
INVENTOR(S)   : Thomas H. Baum et al.

It is certified that error appears in the above-identified patent and that said Letters Patent is hereby corrected as shown below:

Column 6,
Lines 45-46, cancel the word "fluoralkyl" and substitute -- fluoroalkyl --;

Column 7,
Line 20, cancel the word "nitrites" and substitute -- nitriles --;

Column 10,
Line 14, cancel "(hfac)In(II)(CH$_3$)$_2$" and substitute -- (hfac)In(III)(CH$_3$)$_2$ --;

Column 12,
Line 11, cancel "C$_1$-C$_{16}$ fluoroalkyl" and substitute -- C$_1$-C$_6$ fluoralkyl --.

Signed and Sealed this

Eleventh Day of January, 2005

JON W. DUDAS
*Director of the United States Patent and Trademark Office*